United States Patent [19]

Monreal

[11] Patent Number: 4,865,045
[45] Date of Patent: Sep. 12, 1989

[54] SHOEHORN MEDICAL REFLEX HAMMER

[76] Inventor: F. Javier Monreal, 4242 Barker Hill Rd., Jamesville, N.Y. 13078

[21] Appl. No.: 194,506

[22] Filed: May 16, 1988

[51] Int. Cl.[4] .................................................. A61B 5/10
[52] U.S. Cl. .................................... 128/740; 128/744; 223/118
[58] Field of Search .................................. 128/739–740, 128/744, 774, 782, 54; 223/118–119

[56] References Cited

U.S. PATENT DOCUMENTS

| 594,894 | 12/1897 | Nylander | 223/118 |
|---|---|---|---|
| 1,269,820 | 6/1918 | Karatsu | 128/744 |
| 2,532,093 | 11/1950 | Golub et al. | 128/740 |
| 2,908,268 | 10/1959 | Guest | 128/744 X |
| 3,185,146 | 5/1965 | Leopoldi | 128/744 X |
| 3,344,781 | 10/1967 | Allen | 128/744 X |
| 3,515,125 | 6/1970 | Ruskin | 128/740 |
| 4,007,928 | 2/1977 | Doubt | 223/118 X |

FOREIGN PATENT DOCUMENTS 0814426 6/1959 United Kingdom ................ 223/118

Primary Examiner—Angela D. Sykes

[57] ABSTRACT

A medical examination reflex hammer is described having a head and a handle. Its head is a fully spherical, solid rubber ball. Its handle is a long, light weight, cylindrical stem that pierces with a sharp point at one end the ball and at the other end it forms a flattened and slightly concave shoehorn.

2 Claims, 1 Drawing Sheet

SHOEHORN MEDICAL REFLEX HAMMER

BACKGROUND OF THE INVENTION

The purpose of this patent application is to demonstrate a very practical, well balanced, toy-like in appearance but serious and professional, medical examination hammer as used by physicians specially neurologists. A neurologist will generally check with the same tool the deep tendon reflexes of the patient and the plantar responses (the "Babinski reflex") so his hammer has to have a good swing and balance (by having a long and light handle and a relatively heavy rubber head) and a sharp point to check for "Babinskies". Often the surgical-looking tool will scare young or apprehensive patients, so a colorful and toy-like appearance will made the examination easier for many patients. After checking the Achilles reflex and the plantar response the physician may try to help his patient with his shoes and having a handy shoehorn then and there would be most helpful, so in this invention this physician has shaped the end of the handle as a shoehorn for that very purpose, leaving the sharp point at the opposite end beyond the hammer's head (which consists of a solid rubber ball pierced by the pointy handle). The ball is provided in bright and attractive colors and renders itself as an appropriate surface to carry a printed logo or a pharmaceutical/promotional/gift advertisement. The spatula-like shoehorn end also allows similar markings.

Review of existing art work reveals many different reflex hammers, all esentially having a handle or a stem and a rubber head or just a T-shape where the rubber is only at the tips of the cross-bar. Medical hammers used in the US have a triangular, axe-like rubber head and a 7"–8" chromed metal handle. They are compact and easily carried in a coat pocket but are poorly balanced due to their small dimension and overly light head; the result is a clumsy swing and ineffective "hammer action". Some of these hammers, with roughly the same size especially supplied as gift packs or as part or a travel case, contain a length-wise parted handle so the hammer doubles as a tunning fork. Others add to this idea a turning pinwheel (for sensory testing), and others, by making the stem semi-hollow add a testing pin and a fine brush. Again, all these hammers with a variable number of gadgets added, perform poorly as hammers (which ironically was their primary use) as they have no good swing due to lack of dimensions and proper distribution of weight. Often their rubber tips are too small or too hard and the result is that they actually hurt the patient when used.

The reflex "English hammer" is in a class apart as it is long enough, has a light plastic handle and a wheel-with-a-rubber-tire as a head so it has a perfect swing and action. It lacks, however of the conveniences and inoffensive appearance of the hammer proposed in this invention.

This inventor-physician strongly believes that his herein proposed Shoehorn Medical Reflex Hammer is substantially different from all those available and that beyond being a hammer with head and handle as all the others, that it differs from them not just in design and cosmetic appearance, but in its purpose, function and practicality.

BRIEF DESCRIPTION OF THE INVENTION

A medical examination (of the deep tendon reflexes) hammer is described, having, as any hammer, a head and a handle. The handle or stem is long, narrow and cylindrical it is also of light weight. This handle is attached at one end to the head and its opposite end is fanned out and flattened with a slight concavity to form a shoe-horn. The head of this hammer consists of a solid rubber ball, relatively dense and heavy but easily squeezable. The handle is attached to the head by piercing the ball through its center. The weight distribution and length of handle is such that the center of gravity of the whole hammer is at its handle very close to the ball.

Two models are described. Model 1 contains the shoehorn end of the handle with rounded edges; this model also contains a sharp point just past the ball or head, sharp point that is simply the continuation-through-the-ball of the pointy handle. Model 2 contains no sharp point beyond the ball or head of the hammer, but since the presence of a sharp point somewhere is very practical the fanned out shoehorn ending of the handle is supplied not with rounded but with sharp points.

DETAILED DESCRIPTION OF THE INVENTION

Figure 1:
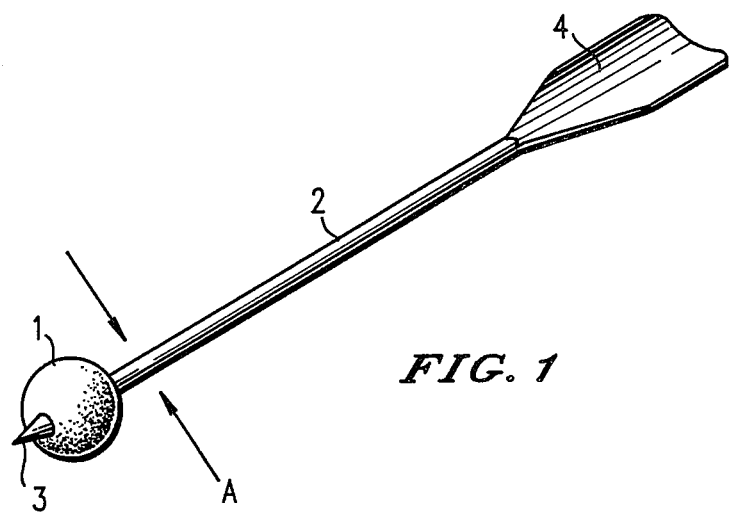
FIG. 1 consists of a three-dimensional view of the instant invention corresponding to model 1 wherein the shoehorn ending has rounded contour and wherein the handle pierces the rubber ball through enough to display, at least for ½" length, a sharp point.

This medical examination instrument is intended to be primarily a reflex hammer to elicit the patient's deep tendon reflexes. As most hammers, medical or not, it has a head and a handle. As all reflex hammers, it has a rubber head to be easy on the patient so it will not hurt as it strikes the knee tendon, Achilles tendon, etc. Its fundamental difference from existing reflex hammers is its fully spherical, soft but solid rubber ball 1, as its head. This ball 1 measures 2" to 2½" in diameter. This ball 1 is pierced by a long and narrow cylindrical stem or handle 2. This handle 2 may pierce the ball completely through with a relatively sharp point that sticks out ½" to 1" beyond the ball. This sharp point 3 is used by the neurologist to scratch the patient's sole of the foot (thus to check for a Babinski sign) and to poke the patient's skin lightly in different areas to test his/her sensory feeling.

The handle 2 is long and light weight and it ends (at the end that the physician grabs) in a widened and flat, semiconcave shoe-horn shape 4. This particular shape allows the examining physician to help the patient put his/her shoes back on after the examination thus aiming at strengthening the patient/physician relationship and bond. The whole handle 2 from its sharp point 3 to its shoehorn ending 4 is of light weight finished wood or nylon or other similar plastic or composite structurally strong fiber, and it should be long enough and light enough as to allow the center of gravity of the hammer to be very near the ball 1, point of gravity marked by the arrow A. Obviously the size of the ball and its weight will determine the length of the handle (i.e. a longer handle per heavier ball).

The ball and the handle (1 and 2 respectively) are supplied in colorful, toy like finish to avoid a surgical and threatening look thus helping the patient to relax.

Figure 2:
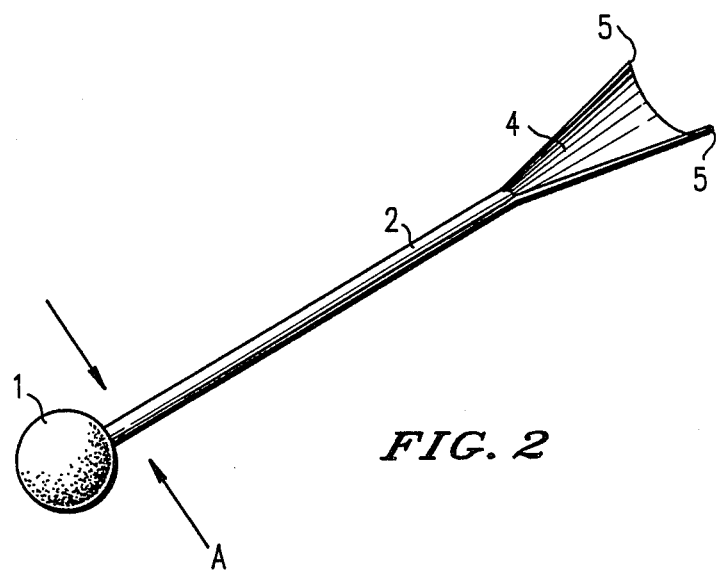
FIG. 2 consists of a three dimensional view of the instant invention corresponding to model 2 wherein the piercing point of the handle does not show beyond the ball and wherein the shoehorn end of the handle, as it fans out, it finishes in two sharp points.

While keeping the essential idea of a reflex hammer-shoehorn combination, a simple variation is offered in FIG. 2 where the essentials of the diameter of the solid ball 1 and the length and weight of the handle 2 and its shoehorn ending 4 are kept as in FIG. 1. In FIG. 2 however, the handle 2 does not pierce the ball 1 completely so the sharp point 3 is eliminated in that location beyond the ball. The overall shape of the shoehorn ending is here modified so instead of having soft rounded edges as in FIG. 1, it has here more isosceles triangle-like shape with straighter edges that come each one to a sharp point 5. These two sharp points 5 and 5 at the ends of the shoehorn serve (as the single sharp point 3 of FIG. 1) to test the sensory feeling and to check for a Babinski sign.

I claim:

1. A hammer medical tool capable of striking gentle but firm blows upon a person's muscle tendon thus eliciting deep tendon reflexes, also capable of stimulating the person's sensory feeling and plantar or Babinski responses, having a head and a handle and such a balance of weight as to have its center of gravity at its handle within an inch or less distance from its head ad comprising:
    a head, fully spherical, two to two-and-a-half inches in diameter of bouncy, firm, solid rubber, having a perforation through its center, the perforation capable of acommodating with a snug fit one end of said handle;
    a handle, of roughly cylindrical shape through almost its entire length, or ¼" to ½" in diameter and of total length such as to provide, in relation to the size and weight of said head, said balance of weight for the whole hammer; said handle having one end tapered to a point and lodged at said perforation of said head; said handle having its opposite end widened, flattened and minimally concaved in a spoon-like or shoehorn-like manner; said handle being of light weight but structurally strong material.

2. A hammer medical tool as in claim #1 wherein the said tapered-to-a-point end of the said handle lodged at said perforation of said head protrudes through and beyond said head ½" to 1".

* * * * *